United States Patent [19]
Hanson

[11] Patent Number: 5,224,858
[45] Date of Patent: Jul. 6, 1993

[54] ORTHODONTIC BRACKETS AND ARCH WIRES FOR USE IN COMBINATION THEREWITH

[75] Inventor: G. Herbert Hanson, Hamilton, Canada

[73] Assignee: Hamilton Ortho Inc., Hamilton, Canada

[21] Appl. No.: 826,737

[22] Filed: Jan. 28, 1992

[51] Int. Cl.$^5$ .............................................. A61C 3/00
[52] U.S. Cl. .......................................... 433/10; 433/20
[58] Field of Search ................ 433/8, 9, 10, 11, 13, 433/14, 15, 17, 20

[56] References Cited

U.S. PATENT DOCUMENTS

| | | | |
|---|---|---|---|
| 3,193,930 | 7/1965 | Bien | 433/15 |
| 3,854,207 | 12/1974 | Wildman | 433/11 |
| 4,050,156 | 9/1977 | Chasanoff et al. | 433/8 |
| 4,424,033 | 1/1984 | Wool | 433/20 |
| 4,731,018 | 3/1988 | Adell | 433/20 |
| 4,818,226 | 4/1989 | Berendt et al. | 433/20 |
| 4,850,865 | 7/1989 | Napolitano | 433/20 |

Primary Examiner—Cary E. O'Connor
Attorney, Agent, or Firm—Rogers & Scott

[57] ABSTRACT

A new orthodontic bracket has a mesial-distal extending labially-open arch wire slot that in gingival-occlusal cross section is curved at its lingual face about a mesial distal axis and has its gingival and occlusial faces which usually are straight smoothly joining the lingual face and extending away from one another to form a slot opening of greater gingival-occlusial dimension. A spring retainer member embraces the gingival, occlusial and labial faces and is movable between a slot open position and a slot closed position, in the latter of which it opposes any protrusion of an arch wire out of the slot caused by misalignment between the slot and the arch wire The retainer is held in the slot closed position by latches which permit a small movement of the retainer away from the fully slot closed position, but which oppose such movement by spring and cam action. In a final stage of the orthodontic procedure the bracket is used with an arch wire of D-cross-section matched at its curved face to the curvature of the slot lingual face; the wire holds the teeth in the desired arch configuration while they are moved along it, anti-tipping forces of suitable low value being produced if the the wire tilts in the slot by spring reaction of the bracket retainer against the wire.

33 Claims, 5 Drawing Sheets

ORTHODONTIC BRACKETS AND ARCH WIRES FOR USE IN COMBINATION THEREWITH

FIELD OF THE INVENTION

The present invention provides new orthodontic brackets of the type having a mesial-distal extending slot for the reception of an arch wire that during the course of an orthodontic procedure connects together a plurality of tooth-mounted brackets. The invention also provides arch wires of new transverse, gingival-occlusial cross-section for use in combination with these new brackets.

REVIEW OF THE PRIOR ART

Orthodontic procedures now almost universally require the attachment of a bracket to each of a plurality of selected teeth, and the connection together of those brackets by an arch wire that applies the desired restoring forces to the misplaced teeth. One technique using such brackets and arch wires is the so-called "edgewise" technique, which is characterised by the use of a bracket having a labially-opening mesial-distal extending slot of rectangular, gingival-occlusial cross-section that receives the arch wire. The wire is also of rectangular transverse cross-section and of a size such that it is a close fit within the slot, so as to be able to apply angular torque to the bracket by engagement of its sides and edges with the walls of the slot.

Another technique known as the "light wire" technique, developed by P. R. Begg, employs a light circular cross-section wire in the rectangular cross-section slot, the moving force being transmitted from the wire to the bracket by an attachment, usually consisting of a ligature that embraces the bracket body and the wire.

Other forms of brackets have been developed which incorporate spring members engageable with the arch wire so as to avoid the need for separate ligatures, such as those disclosed and claimed in my prior U.S. Pat. Nos. 4,248,588 and 4,492,573.

There is also a constant endeavour to provide brackets which are as small as possible, so as to be as inconspicuous as possible, and also to give greater flexibility in their placement on the teeth, which facilitates and simplifies for the orthodontist the procedure to be followed, and which provide for rapid and effective tooth movement with light but relatively constant forces so as to avoid potential deleterious effects such as gum damage and root resorption.

DEFINITION OF THE INVENTION

It is the principal object of the invention to provide a new form of orthodontic bracket.

It is another principal object to provide a new combination of arch wire and orthodontic bracket.

In accordance with the invention there is provided an orthodontic bracket comprising:

a bracket body having mesial, distal, labial, lingual, gingival and occlusal sides;

the bracket body having therein a mesial-distal extending slot with closed sides to the lingual, gingival and occlusal, and open sides to the mesial, distal and labial;

the gingival-occlusial cross-section of which slot is such that its lingual side is concave toward the labial and smoothly curved, its gingival and occlusal sides being smooth extensions of the lingual side; and a resilient retainer member mounted on the body for movement between a slot closed position in which it extends along and closes the slot labial side and is engaged by an arch wire within the slot and protruding through the slot open labial side, and a slot open position in which the slot labial side is open for insertion and removal of an arch wire therein.

Preferably the slot lingual side in the gingival-occlusal cross-section is part circular about a mesial-distal axis.

Preferably also the slot gingival and occlusal sides diverge away from one another toward the open labial side, and may be equally divergent relative to a labial lingual plane parallel to the gingival and occlusal sides. The angle of divergence between this plane and each of the slot gingival and occlusal sides preferably is from 5° to 25°, so that each slot lingual side extends over an arc respectively of from 170° to 130°.

Preferably also the retainer member in a gingival-occlusal plane is of U-shape with the base portion engaging the bracket body labial face and its leg portions engaging the gingival and occlusal faces. The retainer member in a mesial-distal plane may also be of U-shape to have two leaves separated by a central slot and is latched to the bracket body by a pair of latches, one on each leaf of the retainer, the latches being disengaged by movement of the retainer leaves mesially-distally toward one another.

An arch wire used in combination with such a bracket a transverse cross-section that is part circular at the lingual side and flat and rectangular at the gingival, labial and occlusal sides with the lingual side merging smoothly with the gingival and occlusial sides, and more specifically is half square and half circular in such cross-section with the square and circular axes coincident.

DESCRIPTION OF THE DRAWINGS

Particular preferred embodiments of the invention will now be described, by way of example, with reference to the accompanying diagrammatic drawings, wherein.

DESCRIPTION OF THE PREFERRED EMBODIMENTS

Figure 1:
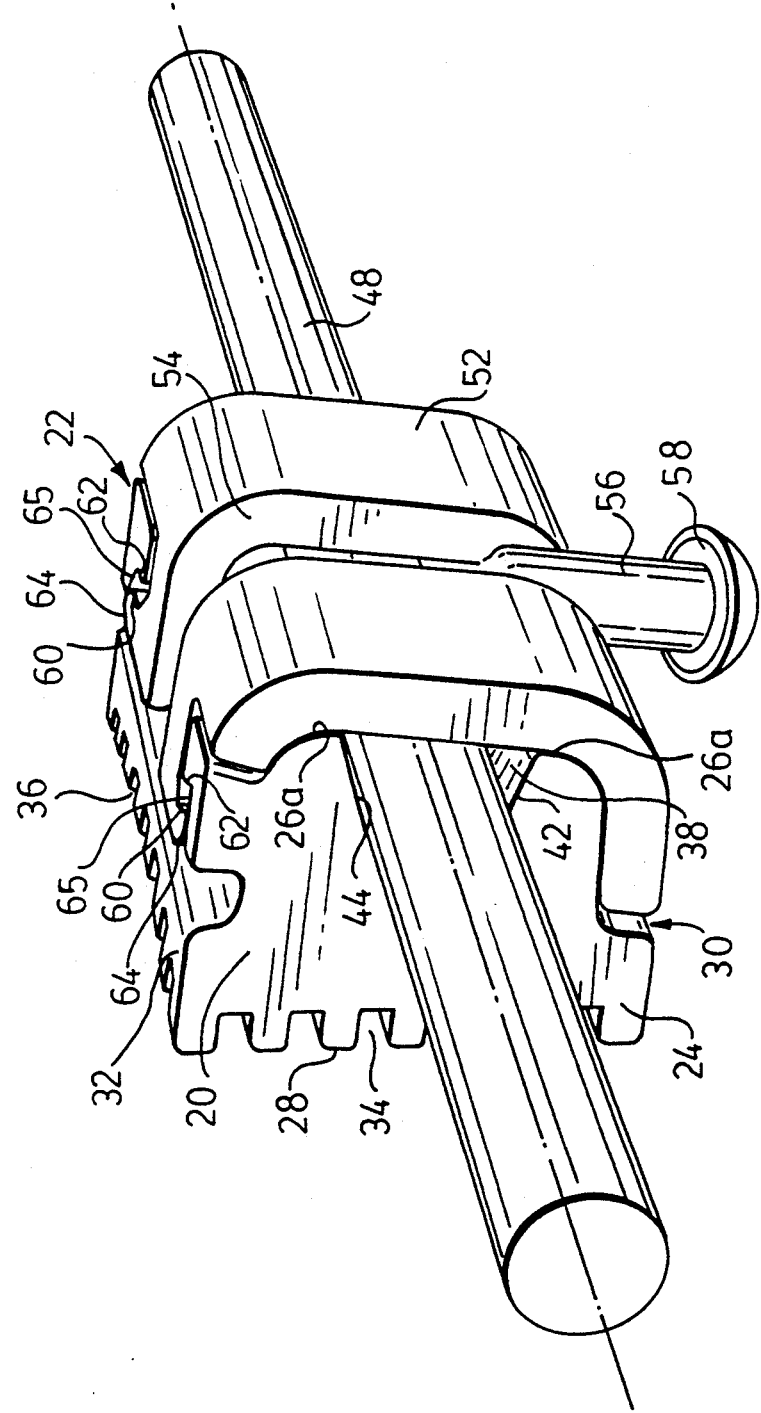
FIG. 1 is a perspective view of a bracket of the invention with a full size round wire in the slot and the spring retainer member in the slot closed position.

In the claims and in the description which follows for convenience and simplicity of language the brackets and arch wire of the invention will be described as if employed in the most usual procedures, namely those in which the brackets are attached to the labial surface of the teeth. They are however also capable of use in the less-used, so-called lingual procedures when the brackets are attached to the lingual teeth surfaces so as to be concealed from view; in such case for example the mesial-distal slot will open to the lingual and not to the labial, and it may also be necessary to reverse the gingival and occlusal surfaces. Again in the interest of simplicity of language the bracket of FIGS. 1-7 will be described as intended for attachment to teeth in the lower arch and the various parts and surfaces will be described in accordance with that convention.

A bracket of the invention consists of a bracket body 20 having (see FIG. 1) mesial, distal, labial, lingual, gingival and occlusial surfaces 22, 24, 26, 28, 30 and 32 respectively. In some embodiments any two adjoining surfaces (such as the mesial and lingual) may merge smoothly into one another without a specific identifiable junction between them. In this embodiment the bracket lingual surface 28 that is to be mounted on the labial surface of a tooth (not illustrated) is provided with a plurality of parallel mesially-distally extending slots 34 and another plurality of gingivally-occlusially extending slots 36 crossing the slots 34 to form a slot grid permitting retention of sufficient cement to securely fasten the bracket to the tooth. This embodiment, and others that together will form a set for use in an individual procedure, is intended for use in the so-called straight wire technique, and accordingly the lingual face is pre-shaped and pre-inclined during manufacture, as is well-known to those skilled in the art, to be used with the specific tooth to which it is to be fastened.

The bracket body is provided with a mesially-distally extending slot 38 having its lingual side 40, gingival side 42 and occlusial side 44 closed, while its labial, mesial and distal sides (unreferenced) are open. As will be seen most clearly from FIGS. 5 and 6, the slot lingual side 40 is concave toward the labial and is smoothly curved, while the gingival and occlusial sides are smooth extensions of the lingual side without specific junctions between them. In this embodiment the gingival and occlusal sides are both flat and they diverge away from one another toward the labial slot side at angles $\beta$ (FIG. 5), which in this embodiment are equal, to a labial-lingual plane 46. During the course of an orthodontic procedure the slot 38 will receive a succession of round cross-section arch wires of increasing diameters, as will be described below, and owing to the spring resilience of these wires they will be urged by that resilience to seek the bottom, or most lingually disposed portion, of the rounded lingual slot surface and, if they are not fully aligned in the slot with their axes of concentricity aligned with that of the slot lingual surface, because of that spring urge, they will apply corresponding moving forces to the bracket until they reach that neutral, aligned bottom slot position. The arch wire 48 shown in FIGS. 1-7 is of the usual maximum diameter that will be employed with this bracket and the curved lingual slot side 40 is formed to be part-circular of a little larger diameter than this particular wire, the preferred dimensions being given below. It may be noted however that in some procedures over-sized diameter wires may also be used at some stage which will not be able to contact the bottom of the slot. Because of this small difference in the diameters there will be little or no frictional resistance to mesial or distal sliding once the bracket and arch wire are aligned with one another. In this embodiment the bottom 50 of the slot 38 is straight between the mesial and distal bracket body ends, and this may be true for all of the brackets of a set. In other sets only the brackets for use with the molars and bicuspids, which are located on the straight parts of the arch wire, will have the slot bottoms straight, and the other brackets will be formed with the slot bottoms on a diameter which corresponds to that of the part of the arch wire arch on which that particular bracket is located.

The second component of the bracket is a retainer member 52 of high tensile spring material, such as a stainless steel, which in a slot closed position shown in FIGS. 1-6 extends over the labial face of the bracket to close the slot labial face. The member 52 is movable between this position and a slot open position illustrated by FIG. 7 in which the arch wires employed can be inserted into and removed from the slot. The member is U-shaped in a mesial-distal plane (see FIGS. 5 and 6) and is formed so that under the effect of its resilience it tightly embraces the labial, gingival and occlusal faces of the bracket body. In the absence of an arch wire protruding from the slot the member presses under its resilience against the two portions 26a of the bracket body labial surface 26 that border the gingival and occlusial edges of the slot mouth. As will be seen from FIGS. 5 and 6, the labial-lingual depth of the slot 38, as measured between these two portions 26a and the bottom 50 of the slot, is equal to the diameter of the wire 48, so that with a wire of this size, or smaller, and with the longitudinal axes of the wire and the slot sufficiently aligned, the retainer is unstrained and abuts the labial wall portions 26a and cannot abut and apply any force to the wire. If however there is misalignment between the wire and slot axes, either in a gingival-occlusial plane or in a mesial-distal plane, or in both, the wire presses against the retainer and attempts to displace it from the unstrained position, causing a spring reaction against the wire and applying a corresponding force to the bracket and to the attached tooth.

The retainer member is of U-shape as seen in plan and front elevation, with a central slot 54 (FIGS. 2-4) that divides it into two coplanar side-by-side leaves, and is positively retained on the bracket body at its gingival end by a gingivally-extending post 56 having a enlarged head 58 that extends through the slot 54. The retained member can pivot on the post about a movable mesial-distal axis that passes through the post, and the length of the post 56 determines the extreme slot open position of the retainer, as shown in in FIG. 7, when tee slot sides contact the head. The post can also serve as an anchor point for a tension member used in the procedure, such as an elastomeric ribbon or other tension spring. The post may increase in diameter from its root towards its head so that movement of the spring leaves down the post forces them to open sideways; it can also be arranged to hold them in the slot open position. The retainer member is latched at its occlusal end to the bracket body by a pair of latches, one on each leaf of the U-shaped member, that are held engaged by the resilience of the member, and also provide a positive bias to urge the retainer into its engagement with the bracket body labial surface. In this embodiment each arm has a mesially or distally extending latch sear member 60, each of which is engageable with a cooperating occlusally and mesially or distally extending latch detent member 62 formed on the occlusal face of the body. The corners 64 of the retainer leaves are curved to constitute ramps, so that the leaves are forced together as the retainer is moved to the slot closed position until the sears can snap under the resultant spring bias into engagement with their respective detents. Similarly, the latches are released when required by squeezing the two arms together, the small size of the bracket usually requiring that this be done by means of a plier- or tweezer-like tool, which is not shown.

Figure 2:
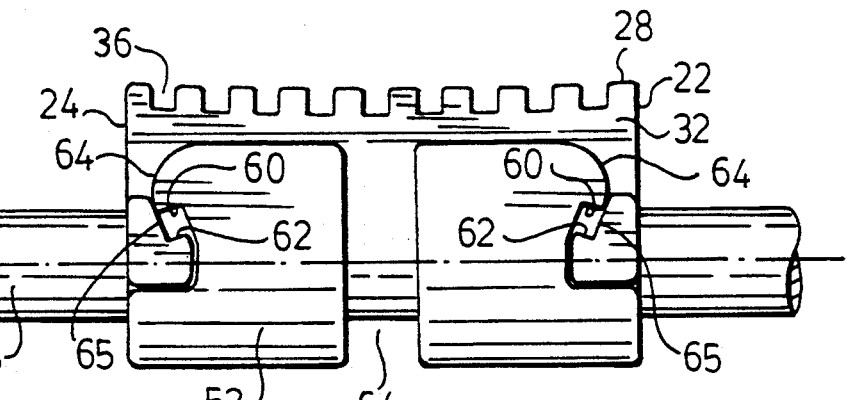
FIG. 2 is a plan view from above of the bracket of FIG. 1.
Figure 3:
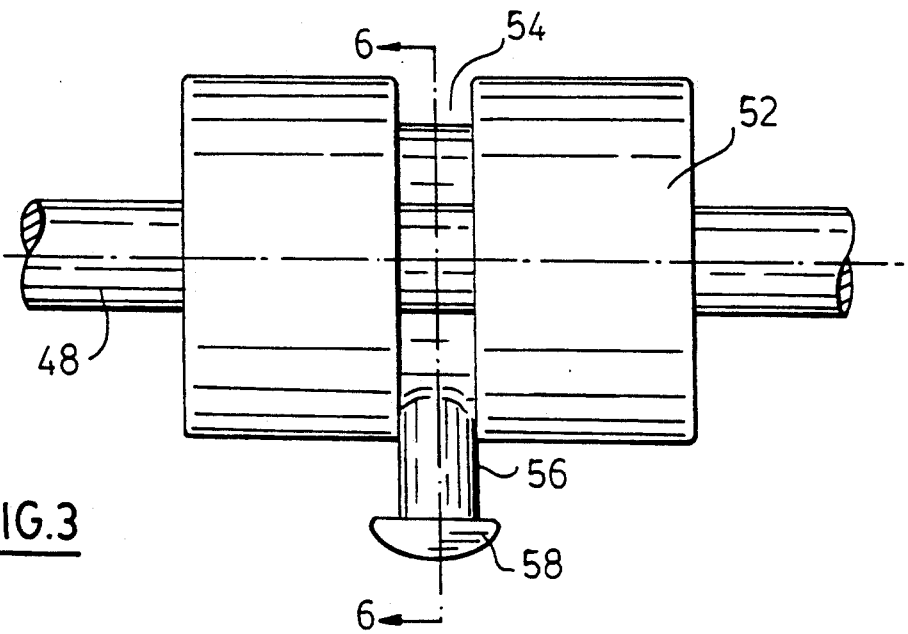
FIG. 3 is a front elevation of the bracket of FIG. 1.
Figure 4:
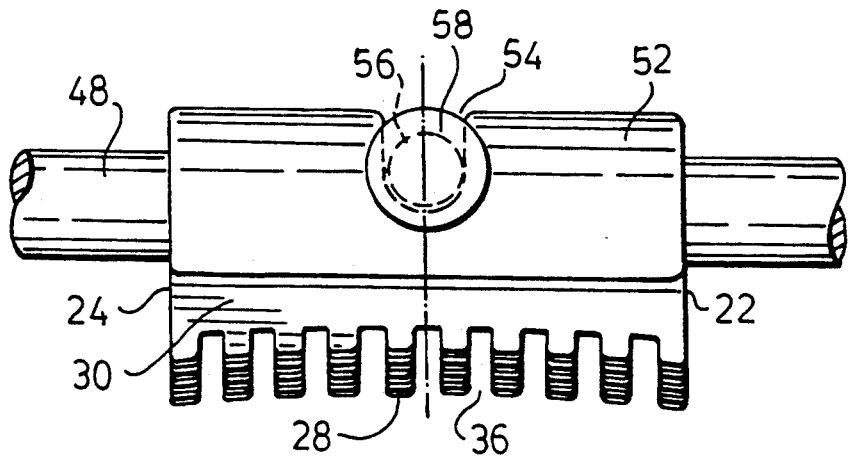
FIG. 4 is a plan view from below of the bracket of FIG. 1.
Figure 5:
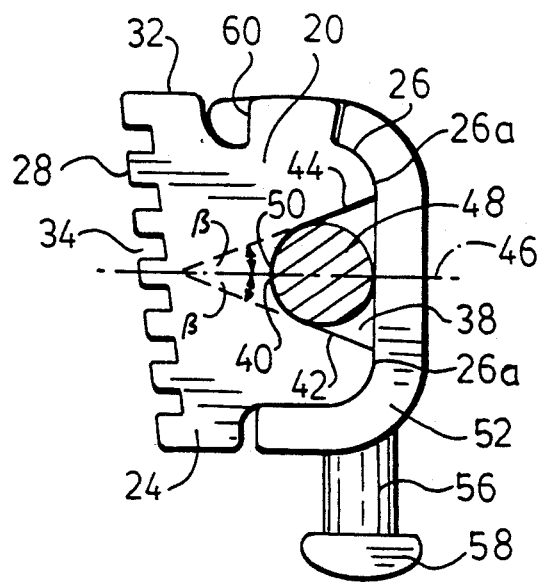
FIG. 5 is a side elevation of the bracket of FIG. 1.
Figure 6:
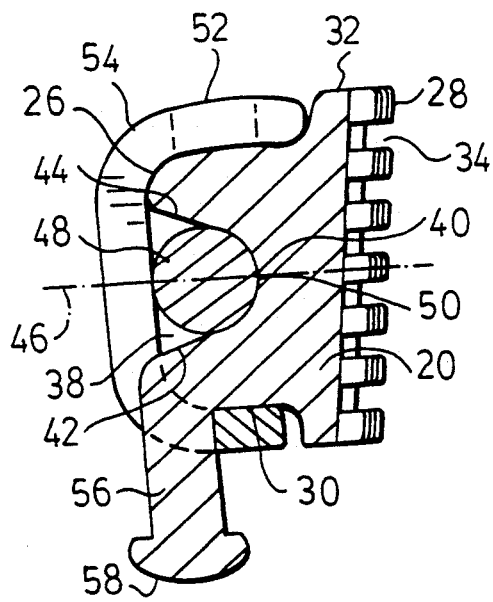
FIG. 6 is a cross-section taken on the line 6—6 of FIG. 3.
Figure 7:
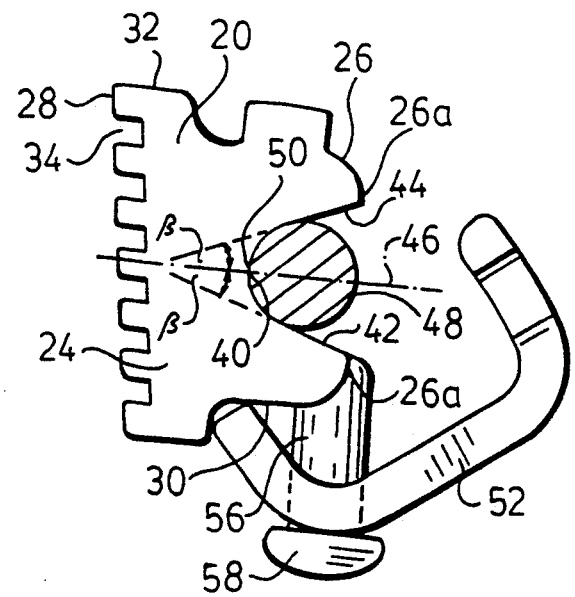
FIG. 7 is a side elevation of the bracket of FIG. 1 showing the arch wire retainer member in its slot open position.
Figure 8:
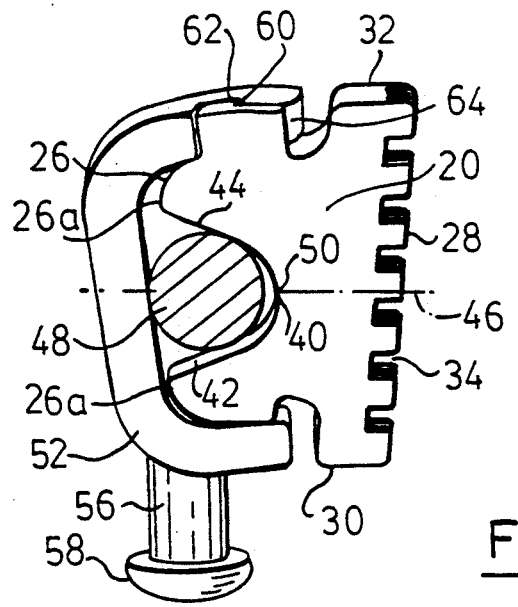
FIG. 8 is a side elevation of the bracket of FIG. 1 and showing the bracket tipped as far as possible about a labial—lingual axis, the Figure also showing the extent to which the retainer member can move upon such misalignment of the arch wire in the arch wire slot before the retainer member latches are engaged.
Figure 11:
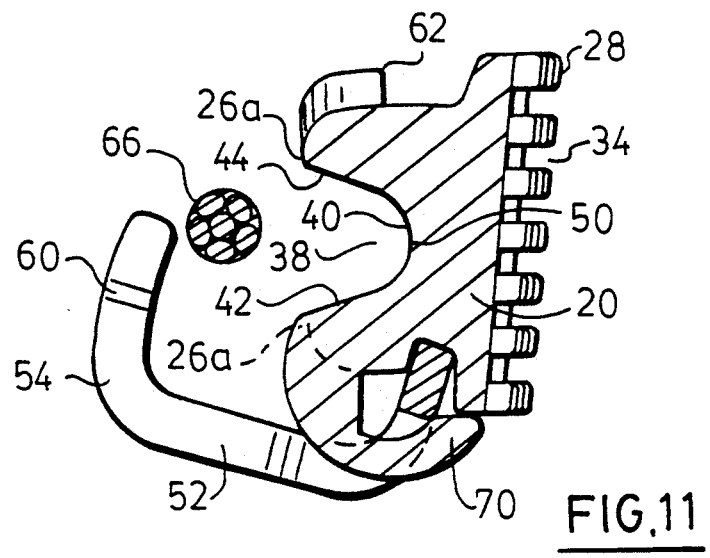
FIG. 11 is a cross-section similar to FIGS. 9 and 10 through another embodiment of the invention, showing the retainer member in the slot open position and showing another type of arch wire as used in the initial stages of an orthodontic procedure.

It will be noted from FIG. 2 that with the retainer snugly butting against the bracket labial surface there is a substantial clearance between the sears 60 and their detents 62. Moreover, the tips of the sears are each in engagement with a respective inclined face 65 of the corresponding detent, the inclination of these faces being toward each other from the lingual to the labial, so that they act in cooperation with their sear tips as ramps urging the retainer leaves in the lingual direction. Thus, any movement of this end of the retainer in the labial direction forces the two leaves together against the inherent resilience of the spring material, so that it opposes any such movement. If the misalignment of the wire in the slot is only small the force applied to the wire by the retainer is correspondingly small, being only that produced by its tight spring embracement on the bracket body and the described cam and spring action as it attempts to maintain its position snugly butted against the bracket body labial face; if there is substantial misalignment such that the latches are fully engaged, as illustrated for example by FIG. 8, then the force applied will be much larger due to distortion of the retainer or of the wire. This arrangement has the advantage that with a stiff wire in the slot the retainer can still move somewhat, for example if the patient bites down hard, to give a small but effective shock absorbing effect. It may be noted that for a bracket used on the upper arch the post 56 may extend gingivally, or it may instead extend occlusally, and in this latter case the latches will be disposed at the gingival face of the bracket body In a typical procedure the brackets are initially connected together by a highly flexible reduced diameter multi-strand arch wire 66, as illustrated by FIG. 11, which although it is substantially smaller than the slot still seeks to align itself with the bottom of the slot, and in so doing applies relatively light moving forces to the brackets. Once the teeth have moved in response to these forces there is a dramatic reduction, approaching zero, in the frictional resistance to sliding of the wire through the brackets. Typically when the large wire 38 is of 0.5 mm 0.020 in) diameter the wire 66 will be of 0.375 mm (0.015 in) diameter. After a period this wire becomes less effective as the teeth are moved, whereupon it is replaced by another highly flexible multi-strand wire of 0.437 mm (0.0175 in) diameter. After another period the multi-strand wire is replaced by a flexible round solid wire 38 of superelastic nickel/titanium and of the usual maximum 0.5 mm (0.020 in) diameter. Other intermediate size and other type wires may also be used as preferred by the orthodontist. When the nickel titanium wire has acted for a sufficient length of time it is replaced by a stiffer solid wire, for example of cobalt/chromium alloy, of the same diameter By use of these different sizes and types of wires the brackets can be made to apply at all times light yet effective moving forces and with minimal frictional resistance to sliding of the brackets along the wire. It is at these later stages of the procedure with the stiffer wires that specific steps are undertaken for movement of the teeth into gaps and extraction sites, usually produced by use of suitable tension springs operative between the brackets.

Figure 9:
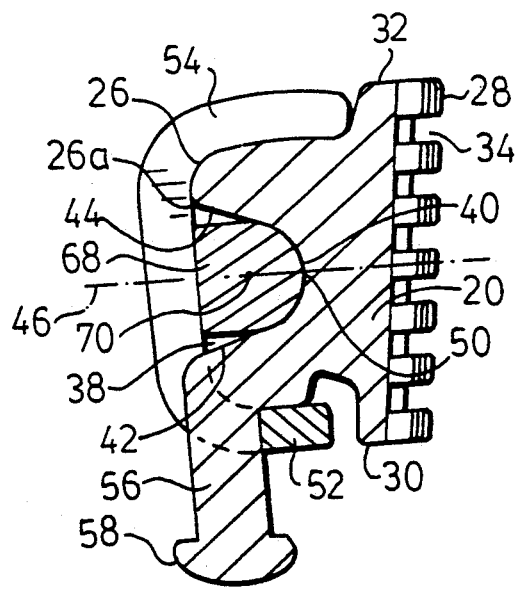
FIG. 9 is a cross-section of the bracket of FIG. 1 in a gingival-occlusial plane and showing its cooperation with a new arch wire of the invention the wire and the bracket being in static equilibrium.
Figure 10:
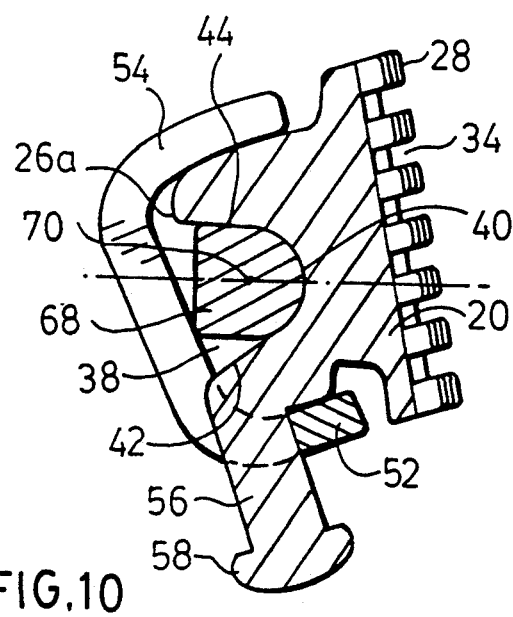
FIG. 10 is a cross section similar to FIG. 9 and showing the cooperation between the new arch wire and the bracket upon misalignment of the wire in the slot, consisting of rotation about a mesial-distal axis away from the equilibrium position of FIG. 9.

By the time that these later stages have been reached all of the badly tilted teeth should have been rendered upright, or very close to their final upright attitudes, and they will also have been rotated to be as close as possible to their desired final positions. During the final stages care must be taken to avoid the possibility that the incisors will tip about the mesial distal axis and/or too far as they are moved lingually This desired effect is produced by use of the D-cross-section arch wire 68 of the invention which, as illustrated by FIGS. 9 and 10, is able to cooperate for the desired action with the outwardly tapered slot 38 of the bracket and with the retainer member in a manner that has not been possible with the rectangular shaped slots used hitherto in these brackets.

The wire transverse cross-section broadly is part circular at its lingual side to cooperate with the circular lingual slot side of somewhat larger diameter, while it is flat and rectangular at its labial, gingival and occlusial sides to cooperate respectively with the flat lingual surface of the retainer member extending between the bracket body labial surface edges bordering the slot, and with the diverging slot gingival and occlusial surfaces, as described below. More specifically its labial, gingival and occlusal sides are all flat and meet at right angle corners (in practice these corners will be slightly rounded). The gingival and occlusal sides merge smoothly into the lingual side which is of the smaller diameter and of greater angular extent than the slot lingual side 40 (i.e. 180° as compared to the preferred value of the slot of 140°). It will also be seen that the cross-section may be regarded as consisting of a half square portion that forms the labial, gingival and occlusal sides and a semi-circular portion that forms the lingual side with the respective longitudinal axes of these two portions coincident. The angular extent of the slot is inherently less than 180° by the value $2\beta$ and preferably therefore is in the range 170° to 130° which corresponds to the preferred range of values of the angles $\beta$, namely from 5° to 25°, with a particular preferred value of 20°. The labial-lingual dimension of the wire from the flat labial face to the peak of the curved lingual face is somewhat less than the diameter of the slot lingual side 40, preferably the same difference as between the slot and the "largest" wire 38, as described above, with the result that if the tooth is in the required upright attitude, so that the axes of cylindricity of the contacting rounded sides are aligned, as illustrated by FIGS. 5–7 and 9, the spring retainer is unstressed and the bracket and tooth can slide relatively freely along the wire with the flat wire labial side parallel to the flat retainer lingual side, and with the tooth held securely in its required attitude. However, if the teeth are tipped, or tend to tip during their lingual movement, then the wire is rotated in their slots, whereupon one or other of the right angle junctions of the labial, gingival and occlusal faces will protrude from the slot and deflect the spring retainer, which will apply the necessary tilting force to the bracket and tooth until the tooth attains the desired attitude. The wire will also be operative to rotate any tooth which still requires any small residual rotation, since this also will involve misalignment of the wire in the slot, and consequent seeking of the wire rounded lingual face to attain the aligned attitude at the bottom of the slot lingual face. The initial tipping and rotating forces obtained are therefore the relatively light forces that result from the embracement of the spring retainer member around the bracket body and the spring camming action between the sear tips 64 and the cam faces 65. This low force spring action of the retainer member is in effect until the gingival face of the wire engages the gingival face of the slot, or vice versa, depending upon the direction of tipping, whereupon the stronger spring action of twisting of the wire would begin. It is arranged however that the rotation of the wire to the extent to engage the wire gingival or occlusial face with its corresponding bracket face is only sufficient to move the retainer latches from the fully spaced position of FIG. 2 to the fully engaged position of FIG. 8, so that the spring force remains within the preferred low range. In practice the potential misalignment of the teeth at this stage is very small, to the extent that it is unlikely that these wire and bracket faces will become engaged. It may be noted that the conventional round wire would be able at this stage to prevent tooth rotation about a gingival-occlusial axis, but is not able to prevent tipping about a mesial-distal axis. The system also permits the use of a very stiff wire, as is desired at this stage of the procedure, to hold the teeth to the required arch, without the danger that this very stiff wire will apply high tipping forces to the teeth roots with consequent possibility of gum, bone and root damage, as is more likely to happen with the conventional rectangular wire operating in a rectangular slot.

Although it is preferred to have the slot gingival and occlusial faces at equal inclinations, since the face to be engaged will change with the arch on which the bracket is employed, the two inclinations do not have the same effect in both directions of rotation, since one of the protruding corners (in this embodiment the corner between the labial and gingival faces) is closer to the pivot than the other, and therefore causes a greater labial displacement of the retainer for a given rotation than the other corner. In some embodiments therefore the inclinations may be unequal so as to compensate for this effect.

Figure 12:
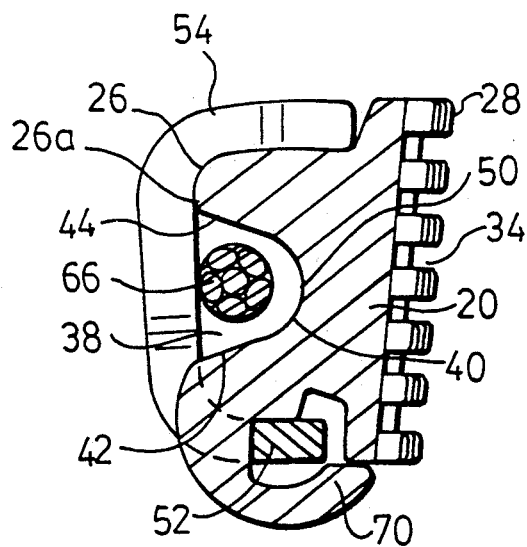
FIG. 12 is a cross-section similar to FIG. 11 showing the retainer member in the slot closed position.

FIGS. 11 and 12 illustrate another embodiment of the invention in which the protruding retainer post is not required, and it is replaced by a curved tongue 70 that extends through the central slot in the spring retainer and presents a smooth external gingival surface, the tongue at the same time retaining the gingival end of the retainer as it moves between the slot open and closed positions.

In a typical embodiment the bracket body is of mesial-distal width from 1.25 mm to 2.5 mm (0.05 to 0.10 in) and of gingival-occlusal height from 2.00 mm to 1.75 mm (0.080 to 0.070 in). The labial-lingual dimension will vary widely owing to the need to form the lingual surface to match the tooth to which it is applied and typically this will be from 1.325 mm to 2.00 mm (0.053 to 0.080 in). As described above, with the preferred embodiment the diameter of the curved arch wire lingual face 40 is 0.50 mm (0.020 in), while the slot lingual face is of 0.55 mm (0.022 in) diameter, even though fullsize wires of 0.55 mm (0.022 in) and oversize wires of 0.6 mm (0.024 in) diameter may sometimes be used therein; such wires are usable because of the tapered cross-section. The stainless steel material used for the spring retainer typically will be of thickness in the range 0.2 mm–0.25 mm (0.008–0.10 in). If the slot lingual faces are curved, as described above, the maximum curvature contemplated is about 16 mm (0.75 in).

For ease of design and economy of manufacture tapering faces 42 and 44 will preferably be flat, as will be the cooperating mating faces of the arch wire, but it will be seen that this is not strictly necessary as long as these faces can engage one another and cooperate together in the manner described for the preferred flat faces.

I claim:

1. The combination of an orthodontic bracket with an arch wire, the orthodontic bracket comprising a bracket body having mesial, distal, labial, lingual, gingival and occlusal sides;

the bracket body having therein a mesial-distal extending slot for reception of the arch wire, the slot having closed sides at the lingual, gingival and occlusal, and open sides at the mesial, distal and labial;

the gingival-occlusal cross-section of the slot being such that is lingual side is concave toward the labial and smoothly curved, its gingival and occlusal sides being smooth extensions of the lingual side; and a resilient retainer member mounted on the body for movement between a slot closed position in which it extends over and closes the slot labial side and will be engaged by a misaligned arch wire within the slot and protruding through the slot open labial side, and a slot open position in which the slot labial side is open for insertion and removal of an arch wire therein;

the arch wire having a transverse cross-section that is convex and smoothly curved at its lingual side and flat and rectangular at its gingival, occlusal and labial sides with the convex smoothly curved lingual side merging smoothly with the gingival and occlusal sides;

the dimension of the convex smoothly curved wire lingual side being smaller than the corresponding dimension of the concave smoothly curved slot lingual side, so that the wire lingual side can engage the slot lingual side; and the lingual labial dimension of the arch wire corresponding to the depth of the slot whereby misalignment of the arch wire in the slot will cause it to attempt to protrude form the slot labial side and to press the wire against the retainer member to attempt to displace the retainer member from an unstrained slot closed position.

2. A combination as claimed in claim 1, wherein the slot gingival and occlusal sides are smooth extensions of the lingual side and diverge away from one another toward the open labial side;

the divergence permitting rotation of the wire in the slot about a slot mesial distal axis with the extent of such rotation limited by engagement of the wire gingival and occlusal sides respectively with the slot gingival and occlusal sides.

3. A combination as claimed in claim 2, wherein the slot gingival and occlusal sides are both straight in the labial-lingual direction.

4. A combination as claimed in claim 2, wherein the slot gingival and occlusal sides are equally divergent relative to a mesial distal plane parallel to the gingival and occlusal sides.

5. A combination as claimed in claim 2, wherein the angle of divergence between a labial lingual plane and the slot gingival and occlusal sides is from 5° to 25°.

6. A combination as claimed in claim 5, wherein the angle of divergence between a labial lingual plane and the slot gingival and occlusal sides if 20°.

7. A combination as claimed in claim 2, wherein the arch wire has a transverse cross-section that is part circular at the lingual side and flat and rectangular at the gingival, labial and occlusal sides with the lingual side merging smoothly with the gingival and occlusal sides.

8. A combination as claimed in claim 7, wherein the arch wire has a transverse cross-section comprising a semi-circular portion at the lingual side and flat and a half square portion at the gingival, labial and occlusal sides with the longitudinal axes of these portions coincident.

9. A combination as claimed in claim 7, wherein the arch wire is of maximum labial-lingual dimension equal to the diameter of the part circular lingual side.

10. A combination as claimed in claim 1, wherein the slot lingual side and the wire lingual side in the respective gingival-occlusal cross-sections are part circular about a mesial-distal axis.

11. A combination as claimed in claim 1, wherein the retainer member in a gingival-occlusal plane is of U-shape with a base portion engaging the bracket body labial face and arm portions at respective ends of the base portion engaging the gingival and occlusal faces.

12. A combination as claimed in claim 11, wherein the retainer member in a mesial-distal plane is also of U-shape to have two leaves separated by a central slot, and wherein the bracket body has a headed post protruding from the gingival face or the occlusal face through the central slot by which the retainer member is retained on the bracket body in the slot open position, the post also guiding the retainer member in its movement between the slot open and closed positions.

13. A combination as claimed in claim 12, wherein the post has a shaft which increases in transverse dimension from its root to its head.

14. A combination as claimed in claim 11, wherein the retainer member in a mesial-distal plane is also of U-shape to have two leaves separated by a central slot, and wherein the bracket body has a tongue protruding rom the gingival face or the occlusal face through the central slot by which the retainer member is retained on the bracket body in the slot open position, the tongue also guiding the retainer member in its movement between the slot open and closed positions.

15. A combination as claimed in claim 11, wherein the retainer member in a mesial-distal plane is also of U-shape to have two leaves separated by a central slot and is latched to the bracket body by a pair of latches, one on each leaf of the retainer, the latches being disengaged by movement of the retainer leaves mesially-distally toward one another.

16. A combination as claimed in claim 15, wherein each latch comprises a sear member on the respective retainer leaf and ac operating detent member on the bracket body and with the retainer member butted closely against the bracket body there is clearance between each sear member and its detent member to permit corresponding movement of the retainer member away from the slot closed position before the latches are engaged.

17. A combination as claimed in claim 15, wherein each latch comprises two cooperating latch members, one latch member having a cam face that is engaged by the other latch member to move the respective retainer member leaf against the resilience thereof and thereby urge the retainer member toward the fully slot closed position.

18. An orthodontic bracket for use with an arch wire, the bracket comprising:
a bracket body having mesial, distal, labial, lingual, gingival and occlusal sides;
the bracket body having therein a mesial-distal extending slot for the reception of the arch wire, the slot having closed sides at the lingual, gingival and occlusal, and open sides at the mesial, distal and labial; and
a resilient retainer member mounted on the body for movement between a slot closed position in which it extends over and closes the slot labial side and will be engaged by a misaligned arch wire within the slot and protruding through the slot open labial side, and a slot open position in which the slot labial side is open for insertion and removal of an arch wire therein;
the retainer member in a gingival-occlusal plane being of U-shape with a base portion engaging the bracket body labial face and with arm portions at respective ends of the base portion engaging the gingival and occlusal faces, and in a mesial-distal plane being also of U-shape to have two leaves separated by a central slot;
the bracket body having a headed post protruding from the gingival face or the occlusal face through the central slot by which the retainer member is retained on the bracket body in the slot open position, the post also guiding the retainer member in its movement between the slot open and closed positions.

19. A bracket as claimed in claim 18, wherein the post has a shaft which increases in transverse dimension from its root to its head.

20. A bracket as claimed in claim 18, wherein the slot in the bracket body is of gingival-occlusal cross section such that its lingual side is concave toward the labial and smoothly curved, its gingival and occlusal sides being smooth extensions of the lingual side and diverging away from one another toward the open labial side.

21. An orthodontic bracket for use with an arch wire, the bracket comprising:
a bracket body having mesial, distal, labial, lingual, gingival and occlusal sides;
the bracket body having therein a mesial-distal extending slot for the reception of the arch wire, the slot having closed sides at the lingual, gingival and occlusal, and open sides at the mesial, distal and labial; and
a resilient retainer member mounted on the body for movement between a slot closed position in which it extends over and closes the slot labial side and will be engaged by a misaligned arch wire within the slot and protruding through the slot open labial side, and a slot open position in which the slot labial side is open for insertion and removal of an arch wire therein;

the retainer member in a gingival-occlusal plane being of U-shape with a base portion engaging the bracket body labial face and with arm portions at respective ends of the base portion engaging the gingival and occlusal faces, and in a mesial-distal plane being also of U-shape to have two leaves separated by a central slot;

the bracket body having a headed post protruding from the gingival face or the occlusal face through the central slot by which the retainer member is retained on the bracket body in the slot open position, the post also guiding the retainer member in its movement between the slot open and closed positions.

22. A bracket as claimed in claim 21, wherein the slot in the bracket body is of gingival-occlusal cross section such that its lingual side is concave toward the labial and smoothly curved, its gingival and occlusal sides being smooth extensions of the lingual side and diverging away from one another toward the open labial side.

23. An orthodontic bracket for use with an arch wire, the bracket comprising:

a bracket body having mesial, distal, labial, lingual, gingival and occlusal sides;

the bracket body having therein a mesial-distal extending slot for the reception of the arch wire, the slot having closed sides at the lingual, gingival and occlusal, and open sides at the mesial, distal and labial; and a resilient retainer member mounted on the body for movement between a slot closed position in which it extends over and closes the slot labial side and will be engaged by a misaligned arch wire within the slot and protruding through the slot open labial side, and a slot open position in which the slot labial side is open for insertion and removal of an arch wire therein;

the retainer member in a gingival-occlusal plane being of U-shape with a base portion engaging the bracket body labial face and with arm portions at respective ends of the base portion engaging the gingival and occlusal faces, and in a mesial-distal plane being also of U-shape to have two leaves separated by a central slot;

the retainer member being latched to the bracket body by a pair of latches, one on each leaf of the retainer, the latches being disengaged by movement of the retainer leaves mesially-distally toward one another.

24. A bracket as claimed in claim 23, wherein the slot in the bracket body is of gingival-occlusal cross section such that its lingual side is concave toward the labial and smoothly curved, its gingival and occlusal sides being smooth extensions of the lingual side and diverging away from one another toward the open labial side.

25. A bracket as claimed in claim 23, wherein each latch comprises a sear member on the respective retainer leaf and a cooperating detent member on the bracket body and with the retainer member butted closely against the bracket body there is clearance between each sear member and its detent member to permit corresponding movement of the retainer member away from the slot closed position before the latches are engaged.

26. A bracket as claimed in claim 23, wherein each latch comprises a cam face that is engaged by the respective sear member to move the respective retainer member leaf against the resilience thereof and thereby urge the retainer member toward the fully slot closed position.

27. A bracket as claimed in claim 23, wherein the bracket body has a headed post protruding from the gingival face or the occlusal face through the central slot by which the retainer member is retained on the bracket body in the slot open position, the post also guiding the retainer member in its movement between the slot open and closed positions.

28. A bracket as claimed in claim 27, wherein the post has a shaft which increases in transverse dimension from its root to its head.

29. A bracket as claimed in claim 27, wherein each latch comprises a sear member on the respective retainer leaf and a cooperating detent member on the bracket body and with the retainer member butted closely against the bracket body there is clearance between each sear member and its detent member to permit corresponding movement of the retainer member away from the slot closed position before the latches are engaged.

30. A bracket as claimed in claim 27, wherein each latch comprises a cam face that is engaged by the respective sear member to move the respective retainer member leaf against the resilience thereof and thereby urge the retainer member toward the fully slot closed position.

31. A bracket as claimed in claim 23, wherein the bracket body has a tongue protruding from the gingival face or the occlusal face through the central slot by which the retainer member is retained on the bracket body in the slot open position, the tongue also guiding the retainer member in its movement between the slot open and closed positions.

32. A bracket as claimed in claim 31, wherein each latch comprises a sear member on the respective retainer leaf and a cooperating detent member on the bracket body and with the retainer member butted closely against the bracket body there is clearance between each sear member and its detent member to permit corresponding movement of the retainer member away from the slot closed position before the latches are engaged.

33. A bracket as claimed in claim 31, wherein each latch comprises a cam face that is engaged by the respective sear member to move the respective retainer member leaf against the resilience thereof and thereby urge the retainer member toward the fully slot closed position.

* * * * *